United States Patent [19]

Biswas et al.

[11] Patent Number: 5,337,381
[45] Date of Patent: Aug. 9, 1994

[54] FIBER OPTIC CYLINDRICAL DIFFUSER

[75] Inventors: Dipak R. Biswas, Plainsboro; Anpei Pan, North Plainfield, both of N.J.

[73] Assignee: Fiberguide Industries, Stirling, N.J.

[21] Appl. No.: 7,112

[22] Filed: Jan. 21, 1993

[51] Int. Cl.⁵ .............................................. G02B 23/26
[52] U.S. Cl. ..................................... 385/36; 385/128; 385/901; 385/902
[58] Field of Search .................. 385/31, 33, 36, 38, 385/901, 902, 126, 127, 128; 362/32

[56] References Cited

U.S. PATENT DOCUMENTS

| | | | |
|---|---|---|---|
| 4,660,632 | 4/1987 | McCaughan, Jr. | 350/96.15 |
| 5,074,632 | 12/1991 | Potter | 385/31 |
| 5,119,461 | 6/1992 | Beyer et al. | 385/147 |
| 5,168,538 | 12/1992 | Gillespie | 385/123 |

OTHER PUBLICATIONS

V. Russo, Optical Fibre Delivery Systems for Laser Angioplsty and Laser Treatment of Tumours Lasers in Medical Science vol. 3:207, 1988, pp. 207–209.

*Primary Examiner*—Frank Gonzalez
*Attorney, Agent, or Firm*—Herbert M. Shapiro

[57] ABSTRACT

A fiber optic, cylindrical, light diffuser for medical use includes an unclad distal fiber end where the exposed core end has a conical shape. The core end is enclosed by a sleeve which contacts the clad portion of the fiber only and defines a closed chamber with the distal end of the fiber. The chamber is filled with light diffusing material. The diffuser exhibits highly uniform output light distribution and is capable of carrying relatively high power densities safely.

5 Claims, 2 Drawing Sheets

FIBER OPTIC CYLINDRICAL DIFFUSER

FIELD OF THE INVENTION

This invention relates to a fiber optic apparatus for producing relatively uniform scattered light output, and, more particularly, to a fiber optic cylindrical diffuser which can be used in a biological environment.

BACKGROUND OF THE INVENTION

"Photodynamic Therapy" (PDT) is a term for a common method for the treatment of cancer and in humans and in animals. There are thee types of devices useful in PDT: The fiber optic cylindrical diffuser or "line source" is one of these types and it is to the cylindrical diffuser that this invention is directed.

The fiber optic cylindrical diffuser is characterized by a cylindrical light scattering pattern symmetrical with respect to the central axis of the optical fiber. Such apparatus has been made with an optical fiber having an exposed core portion at one end with a scattering medium coated on the exposed portion. The apparatus also includes an open end tube adhered to the scattering medium on the clad portion. Apparatus of this type was subject to breakage in use and was limited in the amount of optical energy the apparatus was capable of transmitting safely.

U.S. Pat. No. 5,074,632 issued Dec. 24, 1991, discloses a cylindrical diffuser which overcomes the above defficiencies of some extent. The apparatus of that patent includes a colorless sleeve member which adheres to the clad portion of an optical fiber without touching the exposed core portion of the scattering medium coated on that portion. In a preferred embodiment, the sleeve member has a core head which is at a angle to the flat end of the exposed core portion of the fiber and is spaced apart from that end defining an air filled cavity therebetween. In another embodiment, the core head is open.

It has been found that the light distribution patterns produced by cylindrical diffusers of the above-noted types are insufficiently uniform at distances close to the fiber (the near field) and only moderately better at distances further from that (the far field). In addition there is an increasing need for greater uniformity, increased laser power delivery and mechanical strength in such fiber optic diffusers.

BRIEF DESCRIPTION OF THE INVENTION

In accordance with the principles of this invention, the end of the exposed core portion of the optical fiber of a cylindrical diffuser is made conical in shape. Although it is known to modify the shape of a fiber end to vary light distribution (see V. Russo; "Lasers in Medical Science, Vol. 3:207;1988; pp. 207 et seq.), the use of conical shapes at the end of the unclad core portion in a cylindrical diffuser is considered a significant departure from prior art thinking. Such a conical fiber, in the embodiment, is protected by a threaded sleeve contacting the clad portion of the fiber, with the closed conical clad of the sleeve forming a chamber with the end of the unclad core portion where the chamber is filled with a light dispersive medium.

DETAILED DESCRIPTION OF AN ILLUSTRATIVE EMBODIMENT OF THIS INVENTION

Figure 1:
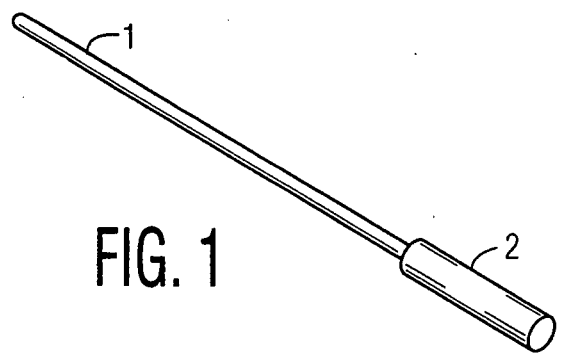
FIG. 1 is a perspective view of a cylindrical fiber optic diffuser.
Figure 2:
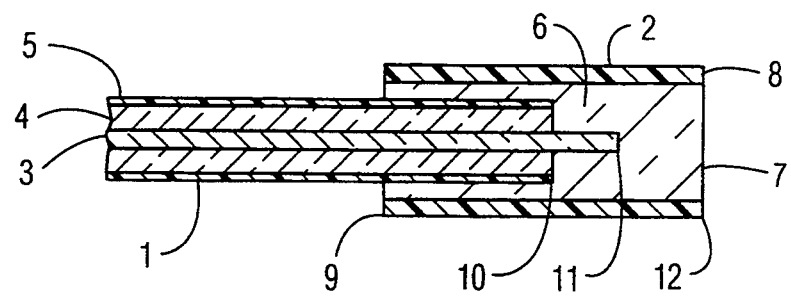
FIG. 2 is a cross sectional view of a prior art cylindrical diffuser useful for the apparatus of FIG. 1.

FIG. 1 shows an optical fiber light conductor 1 with an optical, radiating, light diffuser 2. The diffuser is aligned with the axis of the fiber and attached to the right end of the fiber as viewed. FIG. 2 shows a cross section of a prior art cylindrical diffuser which may serve as the diffuser 2 of FIG. 1. The optical fiber is designated 3 and has a cladding layer 4. The cladding layer has a relatively low index of refraction with respect to that of the core as is well understood in the art. The cladding layer has a protective sheath 5, typically of a plastic material such as polyethylene. The core can be seen to extend to the right beyond the cladding layer and sheathing for a distance typically 1.5 to 3 millimeters.

The region, 6, around the exposed core is filled with light scattering material 7 and the entire structure is surrounded with a protective tube 8, also typically of polyethylene or glass. The diffuser is typically two centimeters long and has an inside diameter of about one millimeter. The dimensions are not critical; but the distance from the upper end 9 of the diffuser to the end 10 of the cladding layer is typically twice as long as the distance between end 10 and the end 11 of the core. The scattering material 7 should provide an uniform cylindrical pattern of light around the circumference of the diffuser. In the prior art diffuser of FIGS. 1 and 2, there is no closed end to the tube 8 at end 12.

Figure 3:
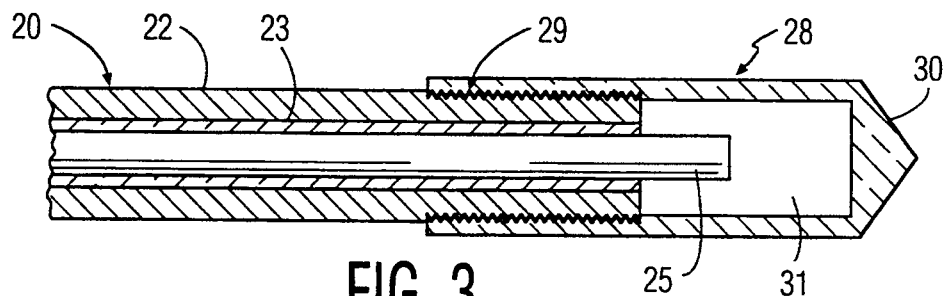
FIG. 3 is a cross sectional view of an alternative prior art cylindrical diffuser also useful in the apparatus of FIG. 1.

That is not the case with the prior art diffuser of FIG. 3. FIG. 3 shows an alternative cylindrical diffuser 20. The diffuser longitudinally positioned optical fiber. The fiber includes a core with a jacket comprising a sheathing 22 and a cladding 23. The core of the fiber is exposed, to the right as viewed, at end 25. A colorless, transparant sleeve 28 is threaded onto the jacket without touching the core. Sleeve 28 includes an open end having an internal thread, at 29, and a closed end 30. The sleeve forms an open chamber 31 about the exposed core.

Figure 4:
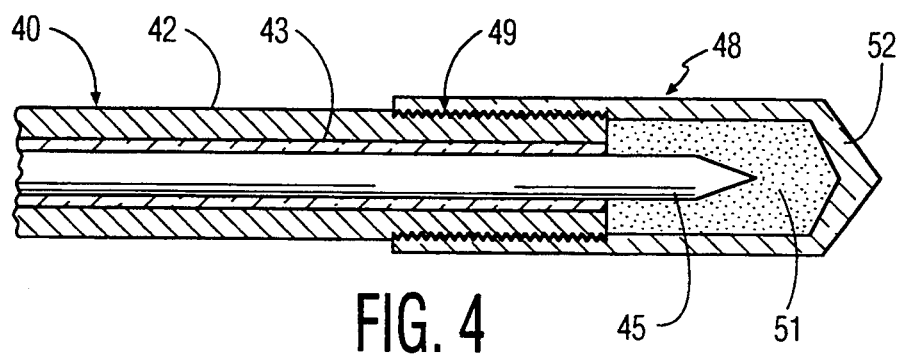
FIG. 4 is a cross sectional view of a cylindrical diffuser in accordance with the principles of this invention which is also useful in the apparatus of FIG. 1.

FIG. 4 shows a cylindrical diffuser 40 in accordance with the principles of this invention. The diffuser of FIG. 4 also includes an optical fiber having an exposed end. The fiber includes a jacket comprising a sheathing 42 and a cladding 43. The right end of the fiber is exposed at 45 and a sleeve 48 attaches to the sheathing 43 via an internal thread at 49. The sleeve forms a chamber 51 surrounding the exposed core end 45.

The exposed end of the core in FIG. 4 can be seen to be conical in shape. Also, the end 52 of sleeve 40 can be seen to be somewhat conical shaped to match the (concentrically positioned) shape of the exposed core end. It has been found that the shape of the core end is important in achieving uniform light distribution, higher power, and handling capability.

In accordance with the principles of the present invention, a fiber optic cylindrical diffuser includes a plastic clad Silica (PCS) optical fiber with a fused Silica core and a cladding of Silicone. The indicies of refraction are, illustratively, 1.458 and 1.41 for the core and the cladding repectively. A protective sheathing of a polymeric material such as Nylon ® or Teflon ® can be used. The core diameter can be varied from between about 125 and 600 microns depending on the requirements of the application for which the diffuser is made.

As can be seen in FIG. 4, the right end of the exposed core is shaped into a conical form. This is accomplished by a grinding, melt and pull technique to produce the conical shape. The sleeve (48) is employed to improve the mechanical properties of the diffuser and to facilitate penetration by the diffuser into tissue or cells. The end 52 of the sleeve also is conical, as stated above, and the chamber (51) formed by the sleeve, the conical end, the bare core, and the ends of the sheathing and the cladding, is filled with polymeric material such as Silicone, epoxy ... etc. with light diffusing material such as Silica, Titanium or Aluminum oxide particles distributed evenly in the polymeric carrier. The chamber is filled prior to threading the sleeve onto the sheath (42).

The use of coaxial, conical core and sleeve ends produce different light propagation parameters and permits the safe transmission of relatively high power when compared to prior art diffusers.

Figure 5:
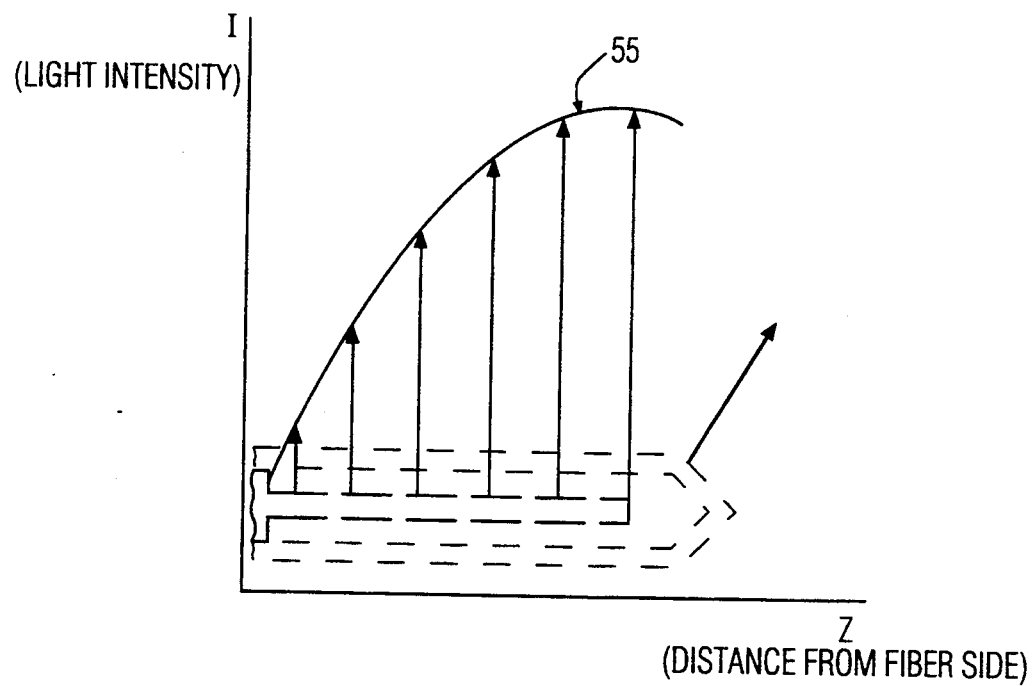
FIGS. 5 and 6 are graphs of light intensity versus position about the diffuser of the prior art and about a diffuser in accordance the principles of this invention, respectfully.
Figure 6:
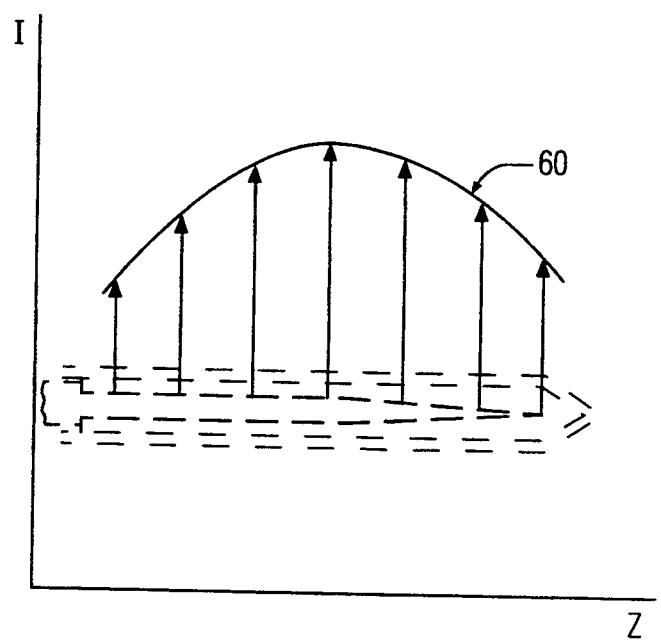

Uniformity of light diffusion is most important for near field applications where the diffuser tip is in contact with (less than one millimeter from) the treated tissue or cells. FIGS. 5 and 6 show representative graphs of light distribution from a prior art diffuser and a like diffuser having conical core and sleeve tip as shown in FIG. 4. Each graph shows a plot of light intensity (I) versus position (Z) about the axis of the diffuser tip. In a prior art diffuser, light emanating from the sides of the exposed core is of significantly lower intensity than the light emanating from the flat tip as can be seen at 55 in FIG. 5. FIG. 6, on the other hand, shows much more uniform light intensity over the entire diffuser as indicated at 60. The light intensity, in each instance, is measured by moving a detector along the exposed core and by measuring the light intensity through a pin hole (one millimeter) aperture. The vertical arrows of different length in the figures represent the different light intensities. The corresponding diffuser is also shown in phantom in each figure for convenience.

As is known, the choice of materials for the fiber core and cladding and for the diffusing material and the dimensions of the various components herein help determine the light diffusion profile of a diffuser. In the diffuser of FIG. 4, the angle of the cone also helps in that determination. For example, for a given choice of materials and dimensions for a particular diffuser, a flat core and sleeve end produces a forward light transmission whereas a right angled conical tip for the same structure produces more sidewise light transmission which helps in cylindrical light diffusion.

Specifically, light distribution around a diffuser tip depends on the thickness of the diffusing material, refractive indicies of Epoxy and diffusing particals, concentration of the diffusing particals and the cone length and angle. Light uniformity for the diffuser of FIG. 6 (measured at 10 millimeters from the tip) varied less than plus or minus 30% from a mean light intensity whereas the uniformity measured from a diffuser of the type shown in FIG. 5 varied more than plus or minus fifty % from the mean intensity.

Further, experimental results indicate that a diffuser can safely transmit power proportionally with increase in core tip surface area. Thus, for example, a flat end diffuser, as shown in figure five, is capable of transmitting safely 1.5 watts of power from a 0.63 micron laser whereas a like diffuser with a conical end, as shown in FIG. 6 safely transmitted over 2.5 watts of power from the same laser.

Light distribution uniformity is important because the light is employed to activate photosensitive chemicals in the human body. Uneven light distribution renders it impossible to quantify appropriate reproducable chemical formulations for light responsive reactions in tissues.

An even further improvement in uniformity of light distribution from a cylindrical diffuser is achieved by shaping the exposed core portion by successive conical steps. Such steps are formed by well understood etching techniques to provide a stepped conical (or Ziggurat) shape (not shown) as viewed in profile. Also, an undulating profile to the core end permits even greater uniformity to be achieved in both the near and far fields.

A glass core of a diffuser can be formed into a conical shape using flame, arc diffusion, mechanical grinding and polishing, and by chemical etching. The steps employed are as follows: First, the cladding is removed and the exposed core is cleaned by Ultrasonic techniques with alcohol. The tip of the exposed core is shaped by flame fusion and by controlled pulling. The tip is inserted into a polymeric housing containing light diffusing materials such as Epoxy, Silicone, or other polymer with a higher refractive index than the glass core and the scattering particles such as Silica, Titanium or Aluminum oxide. The polymer is then cured to adhere to the fiber surface. Cylindrical diffuser tips also can be made with glass cladding on glass cores, as is well understood, and such diffusers also can be made with conical tips in accordance with the principles of this invention.

What is claimed is:

1. A cylindrical light diffuser, said diffuser comprising an optical fiber having first and second ends, said fiber comprising a core and including a cladding for reflecting internally in said core light introduced to said fiber at said first end, said fiber including an unclad portion exposing said core at said second end, said diffuser including a sleeve attached to said fiber at a clad portion thereof adjacent to said unclad portion, said sleeve extending beyond said second end, said second end having a conical shape and wherein said sleeve includes an end portion also having a conical shape.

2. A light diffuser as set forth in claim 1 wherein said conical shape of said second end and said conical shape of said end portion are coaxial and alike.

3. A light diffuser as set forth in claim 2 wherein said sleeve forms a chamber about said unclad portion of said fiber and said chamber has distributed therein light diffusing materials.

4. A light diffuser as set forth in claim 1 wherein said second end of said fiber includes a stepped conical shape.

5. A light diffuser as set forth in claim 1 wherein said second end of said fiber includes an undulating shape.

* * * * *